United States Patent [19]

Ali et al.

[11] 4,339,390

[45] Jul. 13, 1982

[54] PREFERENTIAL IMMUNOREACTIVITY OF SYN-ISOMER OF CORTISOL DERIVATIVE

[75] Inventors: Akhtar Ali, Vernon Hills; Paulus T. K. Tsui, Libertyville, both of Ill.

[73] Assignee: Abbott Laboratories, North Chicago, Ill.

[21] Appl. No.: 235,310

[22] Filed: Feb. 17, 1981

Related U.S. Application Data

[63] Continuation-in-part of Ser. No. 76,648, Sep. 18, 1979, abandoned.

[51] Int. Cl.$^3$ .................................................. C07J 5/00
[52] U.S. Cl. ................................................. 260/397.45
[58] Field of Search ..................... 260/397.45; 424/243

[56] References Cited

U.S. PATENT DOCUMENTS 3,855,208 12/1974 Rutner et al. .................. 260/239.57
3,954,739 5/1976 Wilkinson ....................... 260/239.57

OTHER PUBLICATIONS

"Steroids" vol. 33, No. 1, Jan. 1979, Article by Magyar et al., pp. 47–53.

Primary Examiner—Elbert L. Roberts
Attorney, Agent, or Firm—Steven M. Odre

[57] ABSTRACT

The synthesis, resolution, radiolabeling and determination of the superior immunoreactivity of the syn isomer of a derivative of cortisol-21-acetate is described.

4 Claims, 1 Drawing Figure

PREFERENTIAL IMMUNOREACTIVITY OF SYN-ISOMER OF CORTISOL DERIVATIVE

CROSS-REFERENCE TO RELATED APPLICATION

This application is a continuation-in-part of our earlier application, Ser. No. 076,648, filed Sept. 18, 1979, now abandoned.

BACKGROUND OF THE INVENTION

This invention broadly relates to immunochemical assays and more particularly to radioimmunoassays (RIAs) for the detection and determination of cortisol in a biological sample.

The ability to evaluate the presence of cortisol, an adrenocortisol steroid, is of particular interest to clinicians and researchers alike because of its important role in adrenal cortex functions. It is readily appreciated that an accurate assay for such a physiological component would be extremely valuable in the diagnosis and treatment of a variety of adrenal metabolic disorders.

In radioimmunoassay or competitive protein binding radioassays, the compound to be measured, usually an antigen, is allowed to compete with a similar or chemically related radioactive compound for binding sites on an antibody or on a specific binding protein. Measuring the amount of bound labeled antigen in the standard antibody solution will indicate the amount of targeted compound present in the sample.

Ideally, the antibodies employed should be so specific that they will bind only with the compound or class of compounds to be detected. Often biological fluids contain substances very closely related to the target compound and it is not unusual for antibodies to be unable to distinguish the target compound from closely related metabolites or its congeners.

Just as it is necessary for the antibody to exhibit a high degree of specificity for the target compound, it is important that the antibody exhibit equal affinity for the detectably-labeled compound. Thus, it would be extremely beneficial to prepare a labeled derivative of the target compound which would be indistinguishable from and compete with the target compound for binding sites on the antibody.

Accordingly, it is an object of the invention to provide a method for the synthesis, purification and resolution of stereoisomeric cortisol derivatives.

It is a further object of this invention to provide a method for labeling two stereo-configurationally different cortisol-21-acetate tyrosine methyl esters.

It is an additional object of this invention to provide a reagent useful in immunochemical methods for detecting and determining cortisol in biological samples.

It is the ultimate object of this invention to demonstrate the greater sensitivity and specificity of antibodies for the syn isomer of cortisol-21-acetate tyrosine methyl ester.

SUMMARY OF THE INVENTION

Briefly, the syn and anti-isomers of cortisol-21-acetate-3-iminoxyacetyl tyrosine methyl ester were resolved using thin-layer chromatography. The isomers were radiolabeled with iodine-125 and evaluated for immunoreactivity using antisera generated by the immunization of rabbits with cortisol-21-acetate-3-iminoxyacetic acid covalently linked to bovine serum albumin using water soluble carbodiimide. That antisera demonstrated a significant preference in immunoavidity for the $I^{125}$-labeled syn isomer over either the labeled anti-isomer or the racemic mixture.

DESCRIPTION OF THE PREFERRED EMBODIMENT

Figure 1:
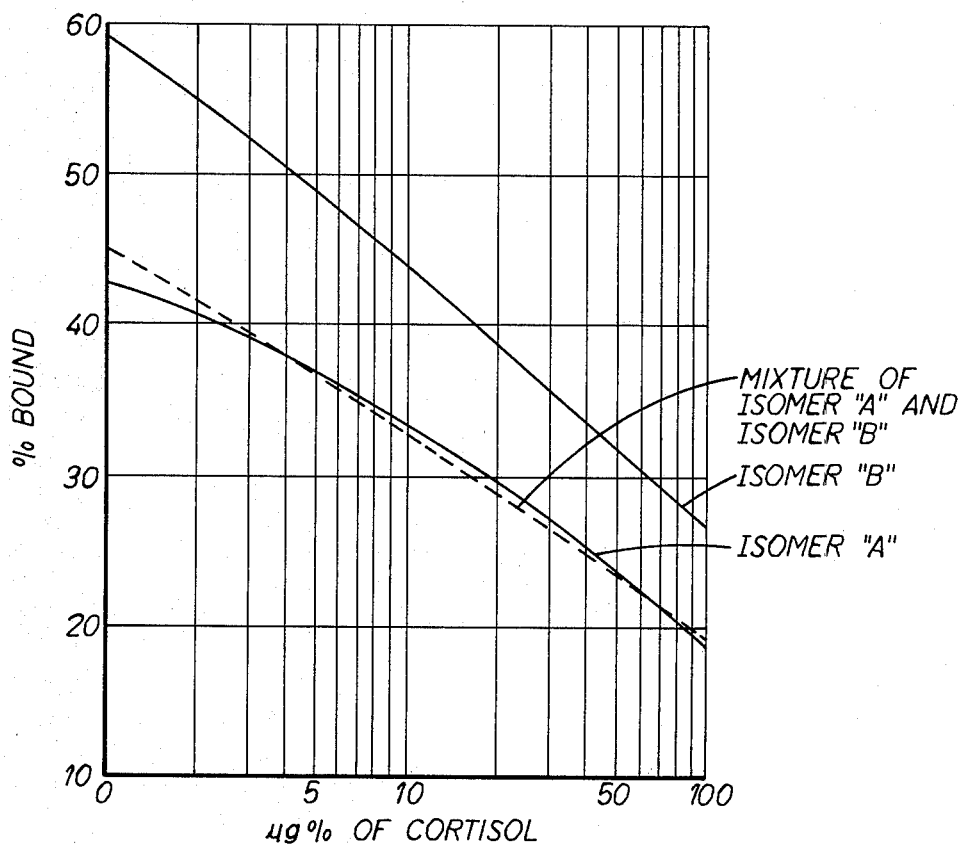
FIG. 1 illustrates the three standard curves generated to show the affinity of antisera for the $I^{125}$-syn isomer, $I^{125}$-anti-isomer and $I^{125}$-mixture (syn and anti). It is apparent from the slope of the curves that the affinity constant calculated is highest when the $I^{125}$ syn isomer is used. As a result, increased sensitivity of the antibody for the $I^{125}$ syn isomer is observed.

The following examples are submitted to demonstrate the objects of the disclosed invention. Example 1 describes the preparation of cortisol-protein conjugate for the generation of antibodies to cortisol-21-acetate.

Since the cortisol molecule alone is unable to produce antibodies when injected into mammals normally used for the generation of antibodies, it is necessary that cortisol be coupled to a compound, usually gamma globulin, capable of eliciting an immune response. To aid in coupling cortisol to a suitable generating substance, it is advantageous to provide the cortisol moiety with a coupling group such as carboxymethyloxime. In fact, cortisol-3-carboxymethyloxime is commercially available from Steraloids, Wilton, New Hampshire.

After a suitable immunogen, such as cortisol-3-carboxymethyloxime-BSA, is produced it is innoculated into mammals commonly recognized for their ability to generate an immune response.

Example 2 demonstrates the synthesis of a cortisol-21-acetate derivative which is designed to be immunologically indistinguishable from cortisol-21-acetate. The derivative should be designed to facilitate the incorporation of the radiolabel. This is usually accomplished by employing cyclic moieties which can be iodinated such as tyrosine, tryamine, histidine; and histamine. Tyrosine methyl ester is utilized in Example 2, but it is readily appreciated that other amino acids, their esters and derivatives thereof could just as easily be employed.

Example 3 demonstrates the radioiodination of the resolved isomers, but it should be apparent that the radiolabel could be isotopes other than radioactive iodine.

Finally, Example 4 describes a competitive radioimmunoassay procedure illustrating the preferential affinity of antibody for the syn-derivative as compared to the anti-isomer or the unresolved mixture.

EXAMPLE 1

PREPARATION OF CORTISOL-21-ACETATE-3-CARBOXYMETHYLOXIME-BOVINE SERUM ALBUMIN

Thirty one mg of 1-ethyl-3,3-dimethylaminopropyl carbodiimide-HCl was added to 62 mg of cortisol-3-carboxymethyloxime in 5 ml of 1:2 concentration of pyridine-dioxane. The mixture was stirred at 4° C. for 0.5 hour and then added dropwise, at room temperature to a 15 ml solution of 105 mg of bovine serum albumin in phosphate buffered saline, pH 7.4. This was stirred at 4° C. overnight. The product was dialyzed against 0.1 M sodium carbonate solution in the cold (3×2 liters). It was then dialyzed against distilled water (3×2 liters) and centrifuged to remove all insoluble materials. The pH of the solution was adjusted to 4.5 with 1.0 N HCl and poured with stirring into four times its own volume of acetone precooled to −20° C. The precipitated protein was washed with water and immediately redissolved with sufficient 0.1 NaOH to bring the pH of the mixture to about 8.0, and all insoluble materials were removed by centrifugation. The supernatant was dialyzed exhaustively against distilled water and lyophilized to a fluffy product (102 mg). Based on spectrophotometric measurements, cortisol-3-carboxymethyloxime-BSA contained 22 cortisol-3-carboxymethyloxime residues per albumin molecule.

Female rabbits were immunized subcutaneously at multiple sites with 1 mg of cortisol-3-CMO-BSA conjugate, prepared according to method of example 1, in saline emulsified with complete Freund's adjuvant (Difco Laboratories, Detroit, Michigan) on weeks 1, 2, 3 and 4 with booster injections of 100 mg of the immunogen being given at longer intervals according to the antibody titer. Blood was collected from the marginal ear vein after three months of immunization. The serum was harvested and frozen for future use.

EXAMPLE 2

CORTISOL-21-ACETATE-3-IMINOXYACETYL TYROSINE METHYL ESTER

Two millimoles (0.95 g) of cortisol-21-acetate-3-CMO, obtained from Steraloid, supra, was mixed with 0.70 g of L-tyrosine methyl ester HCl, 0.23 g of 1-hydroxybenzotriazole, 0.60 g of 1-ethyl-3,3-dimethylamino-propylcarbodiimide-HCl and 10 ml of dry pyridine was stirred at 5°–10° C. for one hour. The solution was then stirred for 20 hours at 15° C. and was evaporated in vacuo at 45° water bath to remove some of the pyridine. Twenty-five ml of water was added and the precipitate was collected on a filter funnel and washed twice with 10 ml of water. The product was dissolved in 50 ml of ethylacetate, washed with water, 50 ml of 1% citric acid solution and again with water. Drying yielded 1.08 g of a solid white cortisol-acetate-3-carboxymethyloxime tyrosine methyl ester. Elemental analyses (C, H, N) and n.m.r. (in CD$_3$OD in 60 MHZ) were in agreement with this structure.

While it was expected that the product should be a mixture of both syn and anti-isomers because of the possible structural configurations of the carboxymethyloxime coupling moiety, TLC plates (silica) in ethyl acetate-ethanol-water-pyridine (95:5:2:1) gave one spot at about Rf 0.78. However, further experimentation with TLC in ethyl acetate alone and in ethyl acetate in toluene (1:1) gave two spots.

The isomers were separated by chromatography using a silica column (180 g) and eluting with ethyl acetatetoluene (3:1). Isomer A was eluted first, and was associated with the faster-moving TLC spot (Rf 0.63 in ethyl acetate). Isomer B gave slower-moving TLC spot (Rf 0.55 in ethyl acetate). Isomer A was more abundant; the ratio being about 7:3 (A:B).

Isomer A is believed to be the anti-oxime isomer having the more extended molecular structure:

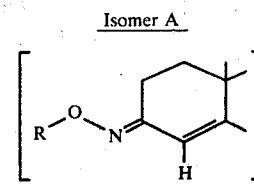

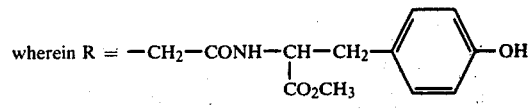

because its n.m.r. spectrum shows the C-4 portion less shielded (at 5.7 ppm is CD$_3$OD solution at 60 MHZ) than is the corresponding proton of the other isomer.

Isomer B, which gave the slower-moving spot on TLC plates (in ethyl acetate), is considered to be the syn-oxime isomer (slightly folded structure which the carboxymethyl group nearer the C-4 proton that its counterpart).

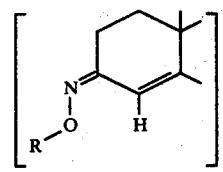

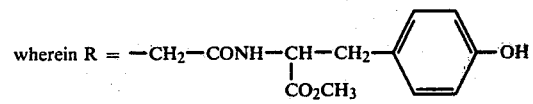

EXAMPLE 3

RADIOIODINATION

Iodinations of the isomers A and B of cortisol-21 acetate-3-CMO-tyrosine methyl esters were performed by the modified procedure of Greenwood, et al, Biochem. J., 89, 114, (1963). To 150 μl of 0.5 M sodium phosphate buffer pH 7.5 was added 35 μl (6.0 mCi) of sodium iodide (I$^{125}$) and 10 μl (5 μg) of cortisol-21-acetate-3-CMO-TME in ethanol. To the reaction mixture was added 50 μl of chloramine-T, 3.5 mg/ml in 0.05 M sodium phosphate buffer pH 7.5 and mixed for 30 seconds at room temperature, followed by the addition of 100 μl of sodium metabisulfite, 3.5 mg/ml in 0.05 M sodium phosphate buffer pH 7.5. The iodination reaction mixture was extracted with ethyl acetate (2×0.5 ml). The combined ethylacetate layer (1.0 ml, 5.3 mCi) was charged to the prepacked, Sephadex LH-20 column (1×17 cm) which was preswollen in absolute ethanol. The column was eluted with an ethanol:pyridine:water 100:0.3:3 solvent system. Fractions of 1.0 ml were collected and 2 to 3 fractions from the radioactive peak were combined and used for assay. The purity of I$^{125}$ cortisol-21-acetate-3-CMO-TME isomers was determined by thin-layer chromatography silica gel plates using ethyl acetate:toluene 50:50 as a solvent system.

After iodinations and purifications, isomers A and B of cortisol-21-acetate-3-CMO-TME gave mostly monoiodo derivatives along with some diiodo derivatives. Specific activities of both isomers were approximately 900–1100 μCi/μg.

EXAMPLE 4

BINDING AFFINITY CURVES

Into appropriately labeled 12×75 mm plastic tubes containing polystyrene beads coated with cortisol antibodies generated according to this disclosure, was added 25 μl of standard serum, followed by 300 μl of radioactive assay solution containing a mixture of borate buffered saline, pH 8.8; 0.12% Triton X 100 and approximately 0.25 ng/ml of either the syn, anti or racemic mixture of $^{125}I$ labeled tyrosine methyl ester derivative of cortisol-21-acetate-3-carboxymethyloxime. The reaction mixture was incubated with agitation at room temperature for one hour. The liquid contents of the tubes were aspirated and the radioactivity bound to the antibody coated beads was counted. The percent bound versus cortisol concentration was plotted. See FIG. 1. It was observed that the antibody had a demonstrably greater affinity for the syn isomer of the labeled antigen conjugate than either the anti isomer or the racemic mixture. Knowing this preference, it would be advantageous in terms of sensitivity and specificity to employ only the syn isomer in assays for the determination of cortisol in biological fluids.

What is claimed is:

1. The syn isomer of a cortisol derivative of the formula:

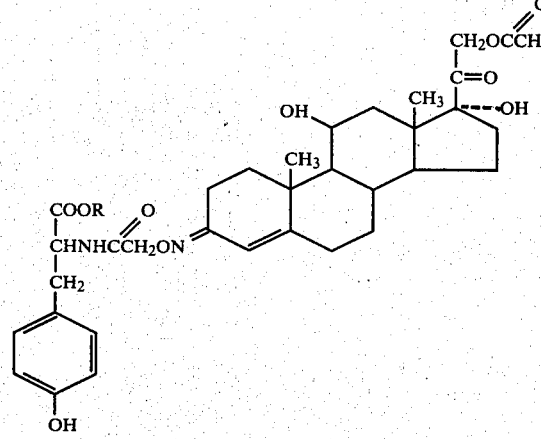

wherein R is selected from the group consisting of hydrogen, methyl and ethyl.

2. The radiolabeled syn isomer of a cortisol derivative of the formula:

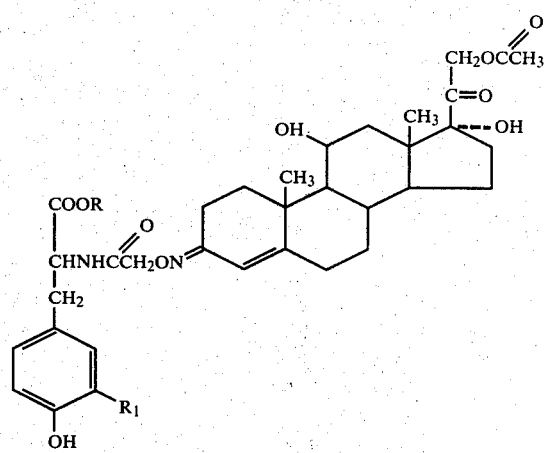

wherein R is selected from the group consisting of hydrogen, methyl and ethyl; and $R_1$ is a radioisotope.

3. The radiolabeled syn isomer of a cortisol derivative of the formula:

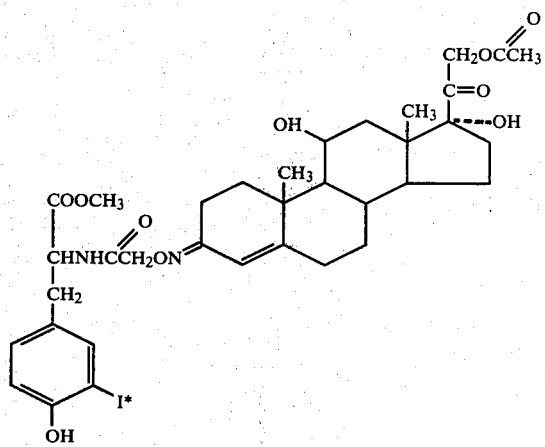

4. The radiolabeled syn isomer of claim 3 wherein the isotope is $I^{125}$.

* * * * *